US012758308B2

(12) United States Patent
Doron et al.

(10) Patent No.: US 12,758,308 B2
(45) Date of Patent: Oct. 13, 2026

(54) POST ABLATION VALIDATION VIA VISUAL SIGNAL

(71) Applicant: Biosense Webster (Israel) Ltd., Yokneam (IL)

(72) Inventors: Itai Doron, Katsir (IL); Konstantin Feldman, Haifa (IL); Hanna Cohen-Sacomsky, Zichron Ya'acov (IL); Gal Bar Zohar, Yokneam Moshava (IL); Lilia Suzdalnitsky, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 401 days.

(21) Appl. No.: 17/138,066

(22) Filed: Dec. 30, 2020

(65) Prior Publication Data

US 2022/0202482 A1 Jun. 30, 2022

(51) Int. Cl.

| | |
|---|---|
| ***A61B 18/14*** | (2006.01) |
| ***A61B 18/00*** | (2006.01) |
| ***A61B 90/00*** | (2016.01) |

(52) U.S. Cl.

CPC .......... *A61B 18/1492* (2013.01); *A61B 90/37* (2016.02); *A61B 90/39* (2016.02);

(Continued)

(58) Field of Classification Search

CPC ..... A61B 18/1492; A61B 18/00; A61B 90/37; A61B 90/39; A61B 2018/00351;

(Continued)

(56) References Cited

U.S. PATENT DOCUMENTS

| | | | | |
|---|---|---|---|---|
| 8,923,959 | B2 | 12/2014 | Boveja et al. | |
| 10,863,915 | B2 * | 12/2020 | Stewart .................. | A61B 5/367 |

(Continued)

FOREIGN PATENT DOCUMENTS

| | | | |
|---|---|---|---|
| CN | 103209654 | A | 7/2013 |
| EP | 2712546 | A1 | 4/2014 |

(Continued)

OTHER PUBLICATIONS

European Search Report for corresponding EPA No. 21218040.0 dated May 18, 2022.

(Continued)

*Primary Examiner* — Beverly M Flanagan
*Assistant Examiner* — Abigail M Ziegler
(74) *Attorney, Agent, or Firm* — Clayton, McKay & Bailey, PC

(57) ABSTRACT

A system and method performed in association with medical equipment in a medical procedure are disclosed. The system and method include measuring at least one electrical signal in the medical procedure, rendering a depiction of the medical procedure on a display, representing the measured at least one electrical signal on the display in conjunction with the rendering of the medical procedure, recording the location of at least one piece of medical equipment during the medical procedure, processing the recorded location of at least one piece of medical equipment, depicting the value of signals measured via the at least one piece of medical equipment, and providing an output that correlates the processed recorded location of at least one piece of medical equipment with the depicted signals measured via the at least one piece of medical equipment at the processed recorded location by the at least one piece of medical equipment.

20 Claims, 5 Drawing Sheets

(52) U.S. Cl.
CPC ............... *A61B 2018/00351* (2013.01); *A61B 2018/00577* (2013.01); *A61B 2090/364* (2016.02)

(58) Field of Classification Search
CPC .... A61B 2018/00577; A61B 2090/364; A61B 5/065; A61B 5/283; A61B 5/339; A61B 5/316
See application file for complete search history.

(56) References Cited

U.S. PATENT DOCUMENTS

| | | | | |
|---|---|---|---|---|
| 2004/0147920 | A1 | 7/2004 | Keidar | |
| 2008/0275440 | A1 | 11/2008 | Kratoska et al. | |
| 2009/0124915 | A1 | 5/2009 | MacAdam | |
| 2009/0204113 | A1 | 8/2009 | Macadam et al. | |
| 2014/0081262 | A1 | 3/2014 | Koblish | |
| 2014/0235989 | A1 | 8/2014 | Wodlinger et al. | |
| 2016/0038047 | A1* | 2/2016 | Urman | A61B 5/367 600/509 |
| 2016/0203608 | A1 | 7/2016 | Izmirli | |
| 2017/0172456 | A1 | 6/2017 | Gliner | |
| 2018/0199990 | A1* | 7/2018 | Monir | A61B 18/1492 |
| 2018/0242868 | A1 | 8/2018 | Cohen et al. | |
| 2019/0008404 | A1 | 1/2019 | Severino | |
| 2019/0038349 | A1* | 2/2019 | Koblish | A61B 90/06 |
| 2019/0099078 | A1 | 4/2019 | Zeidan et al. | |
| 2019/0340837 | A1* | 11/2019 | Shmayahu | A61B 34/10 |
| 2020/0022649 | A1* | 1/2020 | Rodriguez | A61B 5/4878 |
| 2020/0205686 | A1 | 7/2020 | Severino | |
| 2020/0205932 | A1 | 7/2020 | Zar | |
| 2022/0079500 | A1* | 3/2022 | Fishel | A61B 5/7425 |
| 2022/0346867 | A1* | 11/2022 | Harlev | A61B 5/367 |

FOREIGN PATENT DOCUMENTS

| | | | |
|---|---|---|---|
| EP | 4014870 | A1 | 6/2022 |
| JP | 2014018674 | A | 2/2014 |
| JP | 2019063527 | A | 4/2019 |

OTHER PUBLICATIONS

"Biosense Webster Showcases Cutting Edge Innovation At Boston AF 2013" dated Jan. 18, 2023.

Communication of a Notice of Opposition for European Application No. 21218040.0 dated Dec. 16, 2025.

Examiner's Decision of Refusal for Japanese Appiication No. 2021-2140632 dated Jan. 27, 2026.

Notification of Reasons for Refusal for Japanese Application No. 2021-214062 dated Oct. 7, 2025.

Office Action and Search Report for Chinese Application No. 202111657415.2 dated Mar. 26, 2026.

* cited by examiner

POST ABLATION VALIDATION VIA VISUAL SIGNAL

FIELD OF INVENTION

The present invention is related to ablations associated with cardiac arrythmias, and more particularly, to post ablation validation via visual signal.

BACKGROUND

An ablation catheter is often used to ablate heart tissue to prevent electric signals from crossing the ablated tissue. Such a procedure is often performed to prevent atrial fibrillation (AF) often caused by erroneous signals and/or signal sources.

After an ablation procedure has been completed, the effectiveness of the ablation is often verified during a validation period. During the validation period, electrodes of a catheter are placed over areas of ablation and/or areas around the ablation to confirm that electrical signals do not pass through the ablation region. A positive outcome corresponds to the catheter's electrodes reading a flat electrical signal.

During the validation period, a signal graph is provided and includes signals of all catheter's electrodes. When using multi electrode catheters, the signal graph shows the detected signal per electrode. After an effective ablation, the signals detected from the ablation region are supposed to be flat or to show low electrical activity. However, it is often difficult to determine which electrode on the catheter corresponds to the detected signal on the signal graph. For example, a first electrode on a catheter with 8 electrodes may detect a signal that is shown in the signal graph. However, a physician may not be able to easily identify what portion of the organ that signal corresponds to and whether that signal is from within an ablation region or outside the ablation region.

SUMMARY

A system and method for providing a visual representation to a user of a depiction of an organ involved in a medical procedure to show the location where an electrical signal is detected during an operative period, such as a post ablation validation period, for example, is provided.

The system and method performed in association with medical equipment in a medical procedure are disclosed. The system and method include measuring at least one electrical signal in the medical procedure, rendering a depiction of the medical procedure on a display, representing the measured at least one electrical signal on the display in conjunction with the rendering of the medical procedure, recording the location of at least one piece of medical equipment during the medical procedure, processing the recorded location of at least one piece of medical equipment, depicting the value of signals measured via the at least one piece of medical equipment, and providing an output that correlates the processed recorded location of at least one piece of medical equipment with the depicted signals measured via the at least one piece of medical equipment at the processed recorded location by the at least one piece of medical equipment.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION

Figure 1:
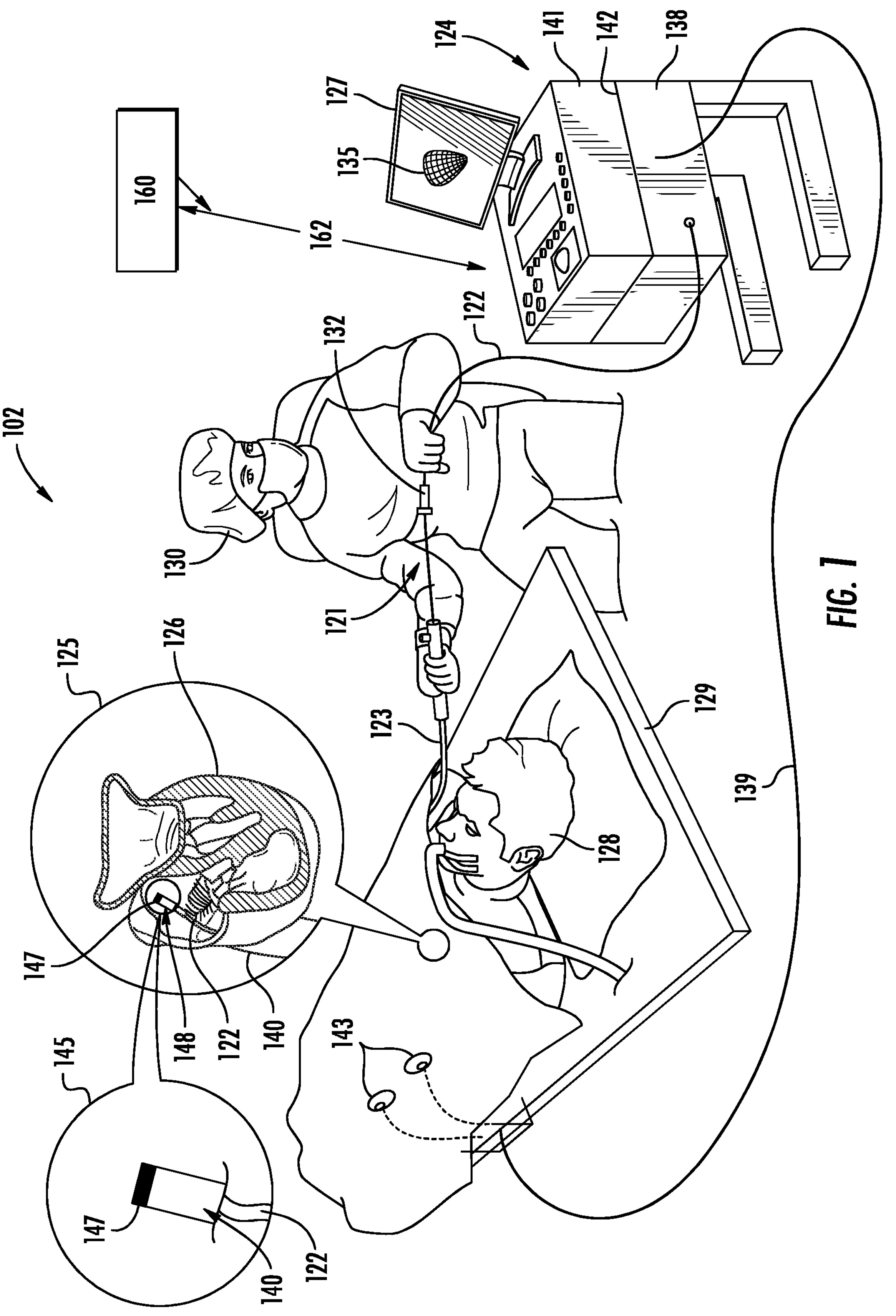
FIG. 1 is a diagram of an exemplary system in which one or more features of the disclosure subject matter can be implemented.

Cardiac arrhythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self-propagating. Alternatively, or in addition to the multiwavelet reentrant type, cardiac arrhythmias may also have a focal origin, such as when an isolated region of tissue in an atrium fires autonomously in a rapid, repetitive fashion. Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

One type of arrhythmia, atrial fibrillation, occurs when the normal electrical impulses generated by the sinoatrial node are overwhelmed by disorganized electrical impulses that originate in the atria and pulmonary veins causing irregular impulses to be conducted to the ventricles. An irregular heartbeat results and may last from minutes to weeks, or even years. Atrial fibrillation (AF) is often a chronic condition that leads to a small increase in the risk of death often due to strokes. Risk increases with age. Approximately 8% of people over 80 having some amount of AF. Atrial fibrillation is often asymptomatic and is not in itself generally life-threatening, but it may result in palpitations, weakness, fainting, chest pain and congestive heart failure. Stroke risk increases during AF because blood may pool and form clots in the poorly contracting atria and the left atrial appendage. The first line of treatment for AF is medication that either slow the heart rate or revert the heart rhythm back to normal. Additionally, persons with AF are often given anticoagulants to protect them from the risk of stroke. The use of such anticoagulants comes with its own risk of internal bleeding. In some patients, medication is not sufficient and their AF is deemed to be drug-refractory, i.e., untreatable with standard pharmacological interventions. Synchronized electrical cardioversion may also be used to convert AF to a normal heart rhythm. Alternatively, AF patients are treated by catheter ablation.

A catheter ablation-based treatment may include mapping the electrical properties of heart tissue, especially the endocardium and the heart volume, and selectively ablating cardiac tissue by application of energy. Cardiac mapping, for example, creating a map of electrical potentials (a voltage map) of the wave propagation along the heart tissue or a map of arrival times (a local time activation (LAT) map) to various tissue located points, may be used for detecting local heart tissue dysfunction Ablations, such as those based on cardiac mapping, can cease or modify the propagation of unwanted electrical signals from one portion of the heart to another.

The ablation process damages the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure—mapping followed by ablation—electrical activity at points within the heart is typically sensed and measured by advancing a catheter containing one or more electrical sensors (or electrodes) into the heart, and acquiring data at a multiplicity of points. These data are then utilized to select the endocardial target areas at which ablation is to be performed.

Cardiac ablation and other cardiac electrophysiological procedures have become increasingly complex as clinicians treat challenging conditions such as atrial fibrillation and ventricular tachycardia. The treatment of complex arrhythmias can now rely on the use of three-dimensional (3D) mapping systems in order to reconstruct the anatomy of the heart chamber of interest.

For example, cardiologists rely upon software such as the Complex Fractionated Atrial Electrograms (CFAE) module of the CARTO®3 3D mapping system, produced by Biosense Webster, Inc. (Diamond Bar, Calif.), to analyze intracardiac EGM signals and determine the ablation points for treatment of a broad range of cardiac conditions, including atypical atrial flutter and ventricular tachycardia.

The 3D maps can provide multiple pieces of information regarding the electrophysiological properties of the tissue that represent the anatomical and functional substrate of these challenging arrhythmias.

Cardiomyopathies with different etiologies (ischemic, dilated cardiomyopathy (DCM), hypertrophic cardiomyopathy (HCM), arrhythmogenic right ventricular dysplasia (ARVD), left ventricular non-compaction (LVNC), etc.) have an identifiable substrate, featured by areas of unhealthy tissue surrounded by areas of normally functioning cardiomyocytes.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical ablation procedure involves the insertion of a catheter having at least one electrode at its distal end, into a heart chamber. A reference electrode is provided, generally taped to the skin of the patient or by means of a second catheter that is positioned in or near the heart. RF (radio frequency) current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficient to cause cellular destruction in the cardiac tissue resulting in formation of a lesion within the cardiac tissue which is electrically non-conductive. During this process, heating of the electrode also occurs as a result of conduction from the heated tissue to the electrode itself. If the electrode temperature becomes sufficiently high, possibly above 60 degrees C., a thin transparent coating of dehydrated blood protein can form on the surface of the electrode. If the temperature continues to rise, this dehydrated layer can become progressively thicker resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs and the catheter must be removed from the body and the tip electrode cleaned.

A system and method performed in association with medical equipment in a medical procedure are disclosed. The system and method include measuring at least one electrical signal in the medical procedure, rendering a depiction of the medical procedure on a display, representing the measured at least one electrical signal on the display in conjunction with the rendering of the medical procedure, recording the location of at least one piece of medical equipment during the medical procedure, processing the recorded location of at least one piece of medical equipment, depicting the value of signals measured via the at least one piece of medical equipment, and providing an output that correlates the processed recorded location of at least one piece of medical equipment with the depicted signals measured via the at least one piece of medical equipment at the processed recorded location by the at least one piece of medical equipment.

FIG. 1 is a diagram of an exemplary system 102 in which one or more features of the disclosure subject matter can be implemented. All or parts of system 102 may be used to collect information for a training dataset and/or all or parts of system 102 may be used to implement a trained model. System 102 may include components, such as a catheter 140, that are configured to damage tissue areas of an intra-body organ. The catheter 140 may also be further configured to obtain biometric data. Although catheter 140 is shown to be a point catheter, it will be understood that a catheter of any shape that includes one or more elements (e.g., electrodes) may be used to implement the embodiments disclosed herein. System 102 includes a probe 121, having shafts that may be navigated by a physician 130 into a body part, such as heart 126, of a patient 128 lying on a bed 129. According to embodiments, multiple probes may be provided, however, for purposes of conciseness, a single probe 121 is described herein but it will be understood that probe 121 may represent multiple probes. As shown in FIG. 1, physician 130 may insert shaft 122 through a sheath 123, while manipulating the distal end of the shafts 122 using a manipulator 132 near the proximal end of the catheter 140 and/or deflection from the sheath 123. As shown in an inset 125, catheter 140 may be fitted at the distal end of shafts 122. Catheter 140 may be inserted through sheath 123 in a collapsed state and may be then expanded within heart 126. Catheter 140 may include at least one ablation electrode 147 and a catheter needle 148, as further disclosed herein.

According to exemplary embodiments, catheter 140 may be configured to ablate tissue areas of a cardiac chamber of heart 126. Inset 145 shows catheter 140 in an enlarged view, inside a cardiac chamber of heart 126. As shown, catheter 140 may include at least one ablation electrode 147 coupled onto the body of the catheter. According to other exemplary embodiments, multiple elements may be connected via splines that form the shape of the catheter 140. One or more other elements (not shown) may be provided and may be any elements configured to ablate or to obtain biometric data and may be electrodes, transducers, or one or more other elements.

According to embodiments disclosed herein, the ablation electrodes, such as electrode 147, may be configured to provide energy to tissue areas of an intra-body organ such as heart 126. The energy may be thermal energy and may cause damage to the tissue area starting from the surface of the tissue area and extending into the thickness of the tissue area.

According to exemplary embodiments disclosed herein, biometric data may include one or more of LATs, electrical activity, topology, bipolar mapping, dominant frequency, impedance, or the like. The local activation time may be a point in time of a threshold activity corresponding to a local activation, calculated based on a normalized initial starting point. Electrical activity may be any applicable electrical signals that may be measured based on one or more thresholds and may be sensed and/or augmented based on signal to noise ratios and/or other filters. A topology may correspond to the physical structure of a body part or a portion of a body part and may correspond to changes in the physical structure relative to different parts of the body part or relative to different body parts. A dominant frequency may be a frequency or a range of frequency that is prevalent at a portion of a body part and may be different in different portions of the same body part. For example, the dominant frequency of a pulmonary vein of a heart may be different than the dominant frequency of the right atrium of the same heart. Impedance may be the resistance measurement at a given area of a body part.

As shown in FIG. 1, the probe 121, and catheter 140 may be connected to a console 124. Console 124 may include a processor 141, such as a general-purpose computer, with suitable front end and interface circuits 138 for transmitting and receiving signals to and from catheter, as well as for controlling the other components of system 102. In some embodiments, processor 141 may be further configured to receive biometric data, such as electrical activity, and determine if a given tissue area conducts electricity. According to an embodiment, the processor may be external to the console 124 and may be located, for example, in the catheter, in an external device, in a mobile device, in a cloud-based device, or may be a standalone processor.

As noted above, processor 141 may include a general-purpose computer, which may be programmed in software to carry out the functions described herein. The software may be downloaded to the general-purpose computer in electronic form, over a network, for example, or it may, alternatively or additionally, be provided and/or stored on non-transitory tangible media, such as magnetic, optical, or electronic memory. The example configuration shown in FIG. 1 may be modified to implement the embodiments disclosed herein. The disclosed embodiments may similarly be applied using other system components and settings. Additionally, system 102 may include additional components, such as elements for sensing electrical activity, wired or wireless connectors, processing and display devices, or the like.

According to an embodiment, a display 127 connected to a processor (e.g., processor 141) may be located at a remote location such as a separate hospital or in separate healthcare provider networks. Additionally, the system 102 may be part of a surgical system that is configured to obtain anatomical and electrical measurements of a patient's organ, such as a heart, and performing a cardiac ablation procedure. An example of such a surgical system is the Carto® system sold by Biosense Webster.

The system 102 may also, and optionally, obtain biometric data such as anatomical measurements of the patient's heart using ultrasound, computed tomography (CT), magnetic resonance imaging (MRI) or other medical imaging techniques known in the art. The system 102 may obtain electrical measurements using catheters, electrocardiograms (EKGs) or other sensors that measure electrical properties of the heart. The biometric data including anatomical and electrical measurements may then be stored in a memory 142 of the mapping system 102, as shown in FIG. 1. The biometric data may be transmitted to the processor 141 from the memory 142. Alternatively, or in addition, the biometric data may be transmitted to a server 160, which may be local or remote, using a network 162.

Network 162 may be any network or system generally known in the art such as an intranet, a local area network (LAN), a wide area network (WAN), a metropolitan area network (MAN), a direct connection or series of connections, a cellular telephone network, or any other network or medium capable of facilitating communication between the mapping system 102 and the server 160. The network 162 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 162.

In some instances, the server 160 may be implemented as a physical server. In other instances, server 160 may be implemented as a virtual server a public cloud computing provider (e.g., Amazon Web Services (AWS)®).

Control console 124 may be connected, by a cable 139, to body surface electrodes 143, which may include adhesive skin patches that are affixed to the patient 128. The processor, in conjunction with a current tracking module, may determine position coordinates of the catheter 140 inside the body part (e.g., heart 126) of a patient. The position coordinates may be based on impedances or electromagnetic fields measured between the body surface electrodes 143 and the electrode 147 or other electromagnetic components of the catheter 140. Additionally, or alternatively, location pads may be located on the surface of bed 129 and may be separate from the bed 129.

Processor 141 may include real-time noise reduction circuitry typically configured as a field programmable gate array (FPGA), followed by an analog-to-digital (A/D) ECG (electrocardiograph) or EMG (electromyogram) signal conversion integrated circuit. The processor 141 may pass the signal from an A/D ECG or EMG circuit to another processor and/or can be programmed to perform one or more functions disclosed herein.

Control console 124 may also include an input/output (I/O) communications interface that enables the control console to transfer signals from, and/or transfer signals to electrode 147.

During a procedure, processor 141 may facilitate the presentation of a body part rendering 135 to physician 130 on a display 127, and store data representing the body part rendering 135 in a memory 142. Memory 142 may comprise any suitable volatile and/or non-volatile memory, such as random-access memory or a hard disk drive. In some embodiments, medical professional 130 may be able to manipulate a body part rendering 135 using one or more input devices such as a touch pad, a mouse, a keyboard, a gesture recognition apparatus, or the like. For example, an input device may be used to change the position of catheter 140 such that rendering 135 is updated. In alternative embodiments, display 127 may include a touchscreen that can be configured to accept inputs from medical professional 130, in addition to presenting a body part rendering 135.

Electrical activity at a point in the heart may be typically measured by advancing a catheter containing an electrical sensor at or near its distal tip to that point in the heart, contacting the tissue with the sensor and acquiring data at that point. One drawback with mapping a cardiac chamber using a catheter containing only a single, distal tip electrode is the long period of time required to accumulate data on a point-by-point basis over the requisite number of points required for a detailed map of the chamber as a whole. Accordingly, multiple-electrode catheters have been developed to simultaneously measure electrical activity at multiple points in the heart chamber.

Figure 2A:
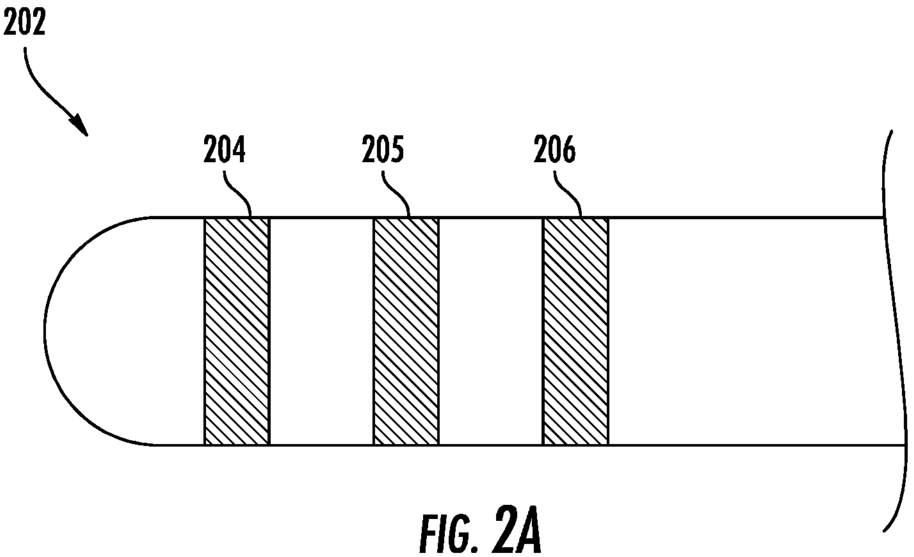
FIG. 2A shows an example of a linear catheter including multiple electrodes that may be used to map a cardiac area.

Multiple-electrode catheters may be implemented using any applicable shape such as a linear catheter with multiple electrodes, a balloon catheter including electrodes dispersed on multiple spines that shape the balloon, a lasso or loop catheter with multiple electrodes, or any other applicable shape. FIG. 2A shows an example of a linear catheter 202 including multiple electrodes 204, 205, and 206 that may be used to map a cardiac area. Linear catheter 202 may be fully or partially elastic such that it can twist, bend, and or otherwise change its shape based on received signal and/or based on application of an external force (e.g., cardiac tissue) on the linear catheter 202.

Figure 2B:
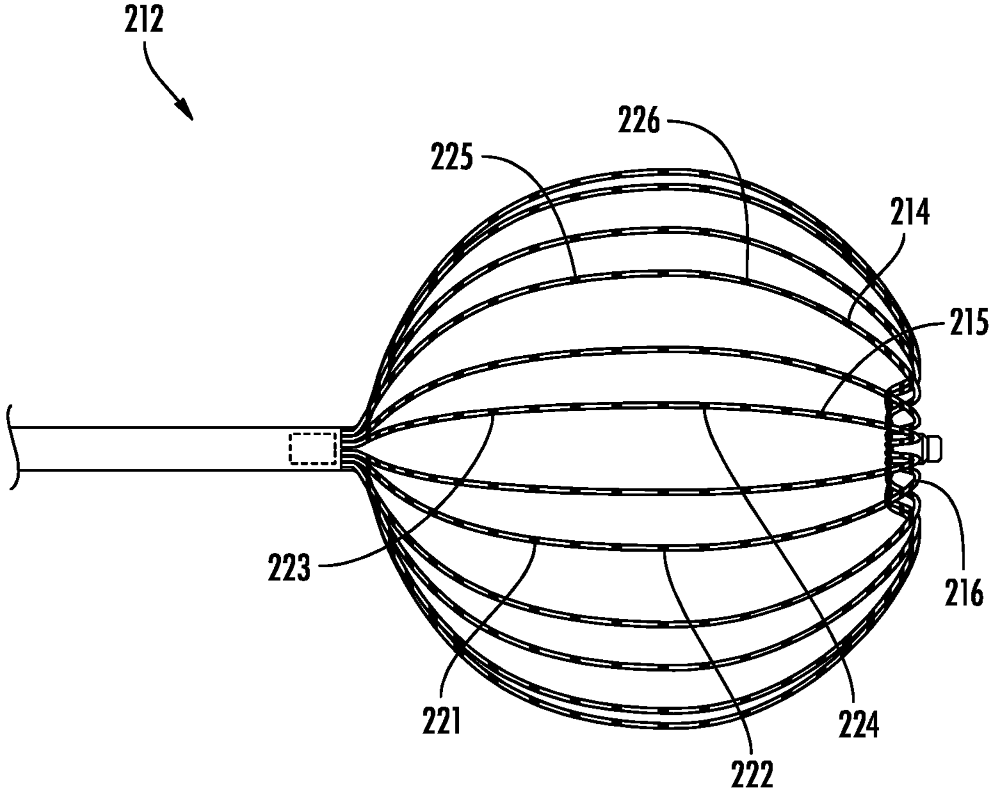
FIG. 2B shows an example balloon catheter including multiple splines and multiple electrodes on each spline.

FIG. 2B shows an example balloon catheter 212 including multiple splines (e.g., 12 splines in the specific example of FIG. 2B) including splines 214, 216, 217 and multiple electrodes on each spline including electrodes 221, 222, 223, 224, 225, and 226 as shown. The balloon catheter 212 may be designed such that when deployed into a patient's body, its electrodes may be held in intimate contact against an endocardial surface. As an example, a balloon catheter may be inserted into a lumen, such as a pulmonary vein (PV). The balloon catheter may be inserted into the PV in a deflated state such that the balloon catheter does not occupy its maximum volume while being inserted into the PV. The balloon catheter may expand while inside the PV such that electrodes on the balloon catheter are in contact with an entire circular section of the PV.

Figure 3:
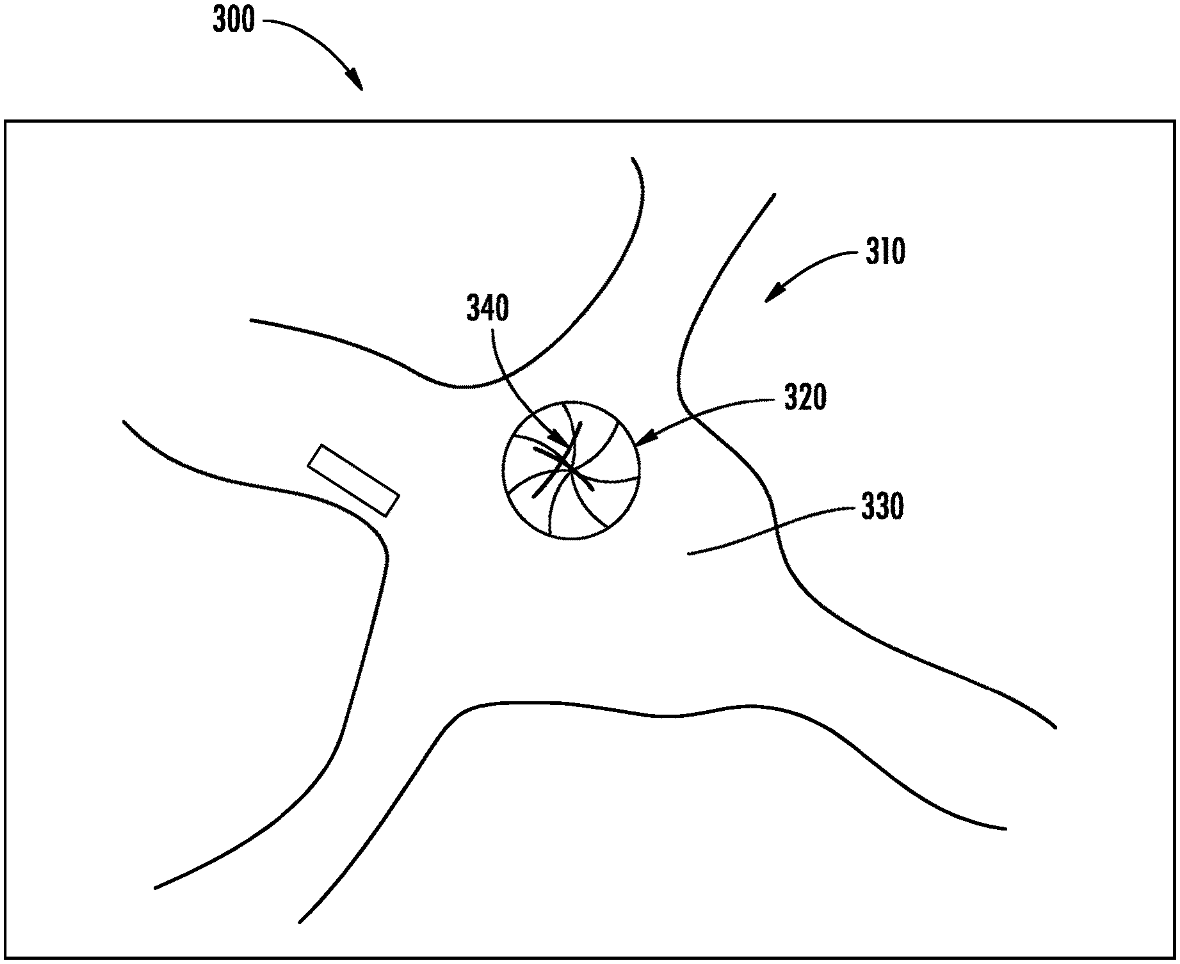
FIG. 3 illustrates a display designed to provide feedback during the validation period of the ablation.

FIG. 3 illustrates a display 300 designed to provide feedback during the validation period of the ablation. A rendering 310 of the organ that is ablated may be provided. Rendering 310 may be provided both during the ablation procedure and during the validation period. Rendering 310 may show an ablated area 330 such that a catheter 320 may be directed to the ablation area 330 during the validation period. The ablation area 330 may include one or more ablations 340. As illustrated, the ablations 340 may include a vertical ablation and a horizontal ablation forming a plus sign. The catheter 320 may contact the ablation area 330 (and possibly ablations 340) to collect any electrical signals that are present in the ablation area. A catheter depiction 320 may be provided in the rendering 310 of the organ.

Figure 4A:
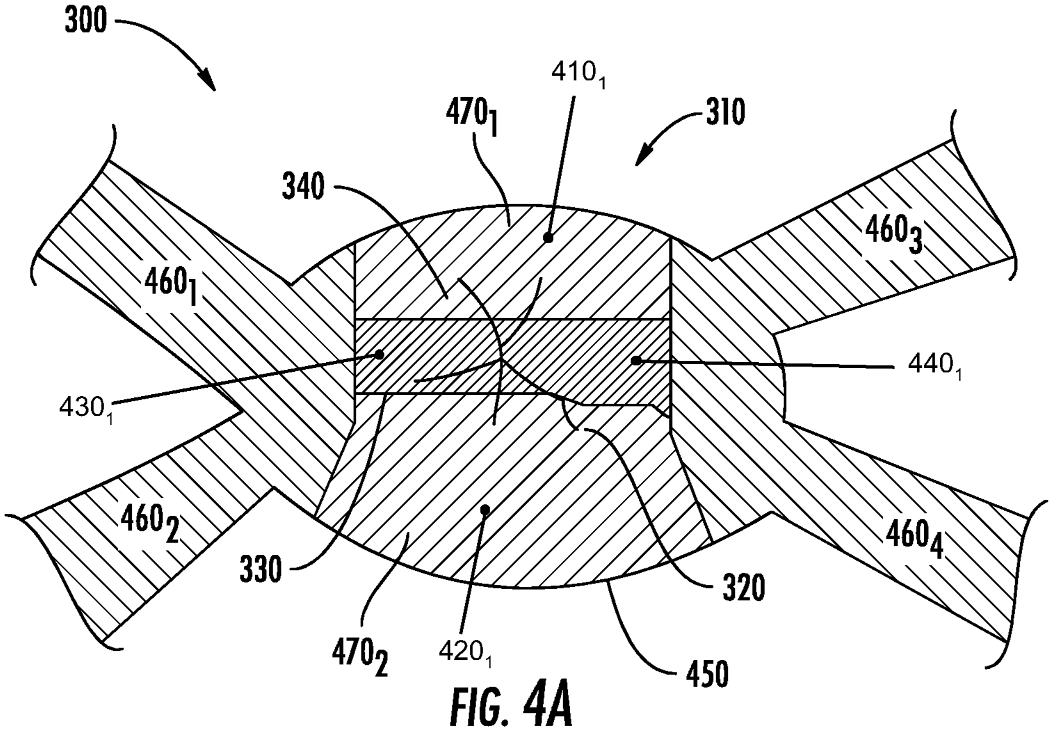
FIG. 4A illustrates a more detailed version of the rendering of FIG. 3 illustrating the display with the heart chamber and the four pulmonary veins, which may be isolated via a pulmonary isolation (PI)

FIG. 4A illustrates a more detailed version of rendering 310 from FIG. 3 illustrating the display 300 with the heart chamber 450 and the four pulmonary veins $\mathbf{460}_1$, $\mathbf{460}_2$, $\mathbf{460}_3$, $\mathbf{460}_4$ (collectively or generically referred to as pulmonary vein 460), which may be isolated via a pulmonary isolation (PI). As described with respect to FIG. 3, there is a catheter 320 in an ablation area 330 having formed one or more ablations 340. As described, the rendering 310 provides a visual indication to allow a physician an identification of the area of the organ where a signal is detected, during the validation period, to determine if additional ablation is necessary. In the organ, the catheter is visualized and over the catheter, the electrodes are visualized.

If a catheter detects a signal with a significant electrical activity (defined by the physician as a threshold), a visual representation such as a light, a marker, a flash, an emphasis, or the like may be visually shown on the electrode visualization of the catheter 320 in the display of FIG. 3 where the signal is detected. Based on the visual representation and the location of the signal, a determination may be made whether the detected signal is within an area 330 that should not have electrical activity or if it is outside such an area in an area, such as area $\mathbf{470}_1$ and area $\mathbf{470}_2$, where good tissue existed and the ablation was not intended to affect the signals in such an area $\mathbf{470}_1$, $\mathbf{470}_2$. If the detected signal is within an area 330 that should not have electrical activity, then additional ablation may be performed.

By way of example, all the electrodes of catheter 320 detecting electrical activity may be presented "green," while those measuring low electrical activity as compared to a threshold may be indicated as "red." Alternatively, or additionally, the electrodes of catheter 320 detecting electrical activity may be presented "constant," while those measuring zero electrical activity as compared to a threshold may be indicated as "blinking."

Figure 4B:
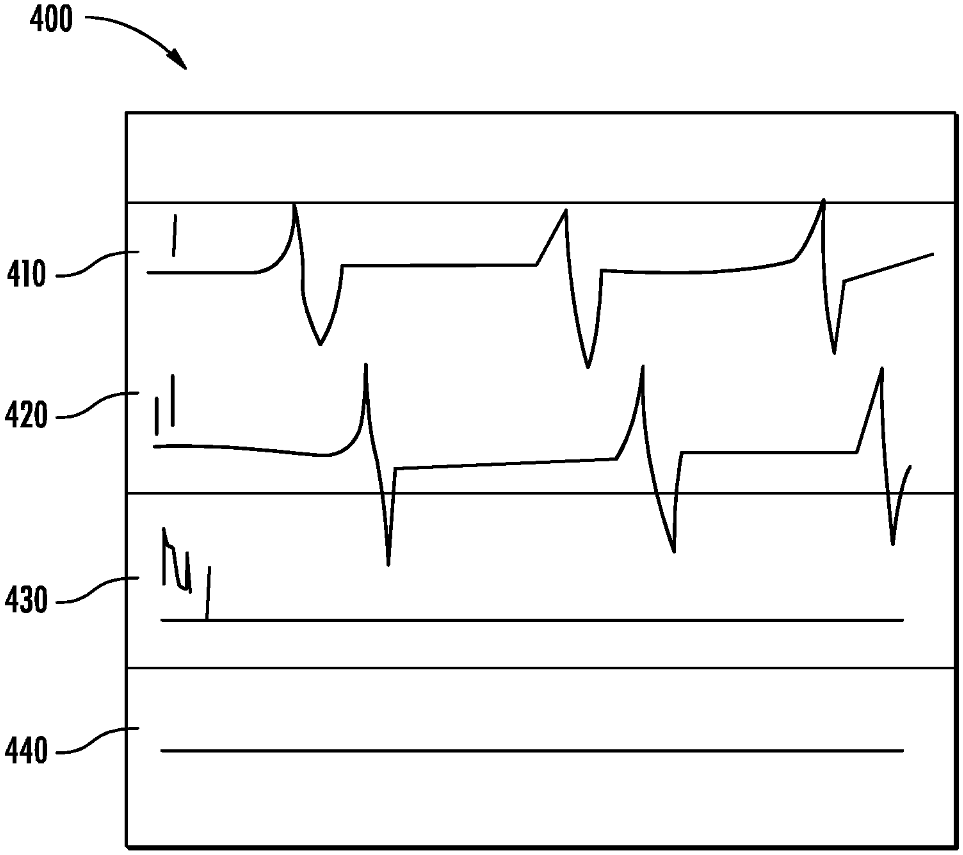
FIG. 4B illustrates a signal graph that may be provided in conjunction with the rendering of FIG. 4A.

FIG. 4B illustrates a signal graph 400 that may be provided in conjunction with rendering 300. Signal graph 400 may illustrate a graph of electrical activity corresponding to all the electrodes of the catheter 320. This may include any number of signals, such as 40 signals for example. The signal graph 400 of FIG. 4B illustrates four such signals, in order to aid in understanding of the present invention. The four signals include signal 1 410, signal 2 420, signal 3 430 and signal 4 440. Each of these signals 1-4 410-440 corresponding to the signal being measured in an electrode of catheter 320. As illustrated, signals 1, 2 410, 430 include electrical activity, while signals 3, 4 430, 440 include no electrical activity or low electrical activity. This may be determined from the signal graph 400.

When the signal (signals 3, 4 430, 440) in display 300 is under a threshold, which can be defined by the user or by BWI, as a no active signal/flat line, this signal which is related to a specific electrode on the catheter 320 can have a visualized indication so the physician may be able to locate that area within rendering 310 and decide if the lack of signal is appropriate or not. When the signal (signals 1, 2 410, 420) in display 300 is above a threshold it may be indicated as an active signal exhibiting electrical activity, this signal which is related to a specific electrode on the catheter 320 can have a visualized indication on the electrode so the physician may be able to locate that area within rendering 310 and decide if having electrical activity is appropriate or not. The rendering 310 of FIG. 4A and signal graph 400 of FIG. 4B are synchronized allowing the location of the catheter electrode and signal visualization to be correlated. This correlation may be achieved by a visual representation, such as a light, a marker, a flash, an emphasis, or the like. That is, the signal graph of an electrode may flash, while the electrode in the rendering also flashes.

The correlation may provide detail when moving the catheter and when interacting with the display. In the situation where the catheter 320 is moving inside the chamber, when the catheter 320 moves, the electrodes within the rendering 310 are visualized as described. For example, where a signal is detected by the catheter 320, the electrodes detecting such a signal may be marked in the rendering 310 with one of the methods specified. As the catheter moves to other places where a signal is detected by the catheter 320, the electrodes detecting such a signal may further be marked in the rendering 310 with one of the methods specified. As the catheter 320 moves and is in a location where the electrodes detect the absence of a signal, the marking of electrodes may cease, or the electrode(s) without a signal may be marked in the rendering 310 distinctively from those electrode(s) marked as having a signal.

Specifically, as the cathode is positioned to measure the electrical signals using an electrode, the measured signal may be plotted. For example, an electrode positioned at location $\mathbf{410}_1$ may provide the signal plot 410, an electrode positioned at location $\mathbf{420}_1$ may provide the signal plot 420, an electrode positioned at location $\mathbf{430}_1$ may provide the signal plot 430, and an electrode positioned at location $\mathbf{440}_1$ may provide the signal plot 440.

As discussed above, when the electrode is at location $\mathbf{410}_1$ with plot 410, the electrode at the location $\mathbf{410}_1$ and the plot 410 may be marked to provide a visual indication to the user that the plot 410 corresponds to the electrode $\mathbf{410}_1$. When the electrode is at location $\mathbf{420}_1$ with plot 420, the electrode at the location $\mathbf{420}_1$ and the plot 420 may be marked to provide a visual indication to the user that the plot 420 corresponds to the electrode $\mathbf{420}_1$. When the electrode is at location $\mathbf{430}_1$ with plot 430, the electrode at the location $\mathbf{430}_1$ and the plot 430 may be marked to provide a visual indication to the user that the plot 430 corresponds to the electrode $\mathbf{430}_1$. When the electrode is at location $\mathbf{440}_1$ with plot 440, the electrode at the location $\mathbf{440}_1$ and the plot 440 may be marked to provide a visual indication to the user that the plot 440 corresponds to the electrode $\mathbf{440}_1$.

Alternatively, or additionally, the present system may operate in reverse from that described above, in that it may react to the user interacting with the display instead of the user interacting with the catheter. In such a configuration, the user may interact with the signal graph 400 via an input device to the display. For example, the graph of the signal in the signal graph 400 may be hovered over with the cursor and the corresponding electrode of the catheter may blink in the rendering 310, or vice versa, such as by hovering over rendering 310 and the corresponding electrical signal blinking. While blinking is provided as one method of providing the user a visual indication, other techniques may additionally, or alternatively, be used. These other techniques may include using coloring, using hashing, flashing, pointers or other method of indicating or providing emphasis or highlight of a depiction in a display.

Alternatively, a single signal on signal graph 400 or electrode on catheter 320 may be selected by user input, for example. That is the depiction may highlight, or present for view, only a single electrode and its corresponding graphical depiction. The corresponding electrode on catheter 320 with signal on signal graph 400 may be presented. While the single signal on signal graph 400 or electrode on catheter 320 is selected, the other signals on signal graph 400 or electrode on catheter 320 may be hidden from view. Similarly, only the corresponding electrode on catheter 320 or signal on signal graph 400 is presented, while the other electrodes on catheter 320 or signals on signal graph 400 may be hidden from view.

By assessing whether the lack of signal, or electrical activity in various areas of rendering 310 by probing with the electrodes of the catheter 320, the physician may determine if additional ablation is required. In essence, the physician may be able to determine if there is unwanted electrical activity within ablation area 330, or if there is unwanted lack of electrical activity outside of ablation area 330 in areas $\mathbf{470}_1$, $\mathbf{470}_2$, for example. If unwanted electrical activity exists within ablation area 330, additional ablation (s) may be performed to control the pathways of such electrical signals. If unwanted lack of electrical activity exists, such lack of electrical activity may indicate that a scar already exists in the chamber, for example. Such a scar may be from a previous procedure, or at least may not be from the present procedure. Such a scar may be a cause of another arrythmia and/or may be of no importance to the present procedure.

Figure 5:
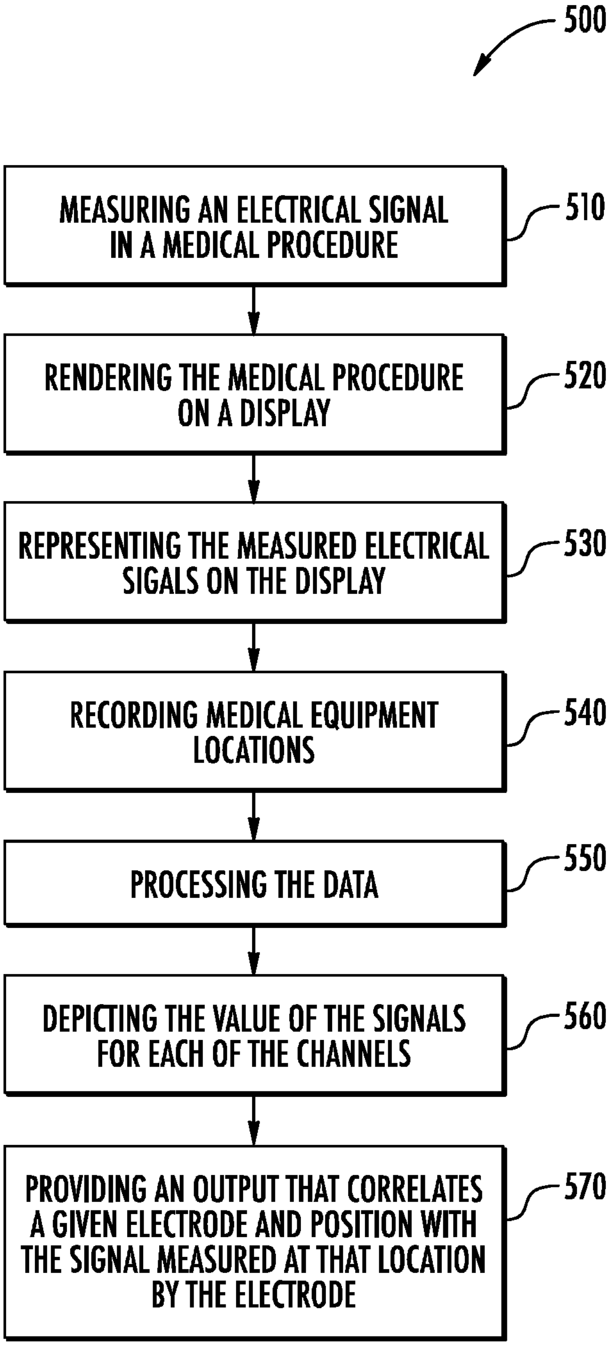
FIG. 5 illustrates a method of providing a rendering of FIG. 3 with correlated signals.

FIG. 5 illustrates a method 500 of providing a rendering of FIG. 3 with correlated signals. Method 500 includes, at step 510, measuring an electrical signal in a medical procedure. At step 520, method 500 includes rendering the medical procedure on a display. At step 530, method 500 includes representing the measured electrical signal on the display. At step 540, method 500 includes recording medical equipment locations, such the catheter locations, for example. In addition, other data of the medical procedure may be recorded including ECG data, force data, and the like. At step 550, method 500 may include processing, which includes analyzing, the data, such as catheter locations and associated electrical signals. This processing may include identifying annotations on the ECG data. As would be understood to those possessing an ordinary skill in the pertinent arts, reference annotation(s) may be included within the data while the procedure is occurring. The processing in step 550 may include detecting or determining the specific channel/s for these mapping annotations and mapping the annotations to the catheter channels. Visualizing or depicting, at step 560, the value of the signals for each of the channels.

If no signal is measured on an electrode, the lack of signal information may be provided to the visualized depiction of that electrode and graph of that electrode's signal may be graphed as a flat line signal. As described above, the lack of signal or flat line may be presented in a number of ways. In short, the electrode and the graph of the signal for the electrode may be colored, or otherwise provided a visual indication allowing a user to notice the electrode, to indicate no signal exists. Visual indications include blinking, marking and the like.

If an ECG signal is measured on another electrode, the signal information, including amplitude, and other commonly understood ECG data, may be provided to the visualized depiction of that another electrode and a graph of that another electrode's signal. As described above, the signal for the electrode may be presented in a number of ways. In short, the electrode and the graph of the signal for the electrode may be colored green to indicate a signal exists.

At step 570, method may include providing an output that correlates a given electrode and its position within the depicted medical procedure with the signal measured at that location by the electrode.

Method 500 may be performed in real-time. The data may be generated and renderer in real-time so when a flat line or signal on the signals is measured it may be simultaneously be depicted the signal/no signal visualization on the 3*d* catheter electrodes model.

In general, the system captures ongoing timeline data and correlates this timeline data with other sensed data. The sensed data may include data sensed by the system, such as ECG, location, and the like. The ECG data may be processed, and using thresholds this processing may identify one or more electrodes as "sensing no ECG data," the identification of these one or more electrodes may then be combined with the location of the catheter at that time of no signal allowing the information to be displayed. A similar, approach may be utilized for the signals above a threshold detected based on catheter location.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random-access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A method performed during a validation period of a medical procedure, the method comprising:

measuring at least one electrical signal during the validation period;

processing a location of at least one device used in the measuring of the at least one electrical signal;

rendering a depiction of the medical procedure during the validation period on a display, the depiction configured to represent a portion of a patient associated with the measured at least one electrical signal, the at least one device, and an area, wherein the area provides an indication of part of the portion of the patient designated to include no electrical activity; and representing the measured at least one electrical signal on the display correlated with the depiction of the medical procedure during the validation period by providing the processed location with a corresponding value of the measured at least one electrical signal, the corresponding value at least indicating a presence or absence of electrical activity at the processed location, wherein the display is configured to provide visual indication to a user of the represented measured at least one electrical signal on the display, the area, and indicating whether the processed location includes electrical activity and is within the area.

2. The method of claim 1 wherein the at least one electrical signal is an electrical signal of a heart.

3. The method of claim 1 wherein the depiction of the medical procedure includes a rendering of a patient heart and a catheter.

4. The method of claim 1 wherein the providing the processed location is performed using a system used for electrophysiological mapping.

5. The method of claim 1 wherein the providing the processed location is performed using a system used for electroanatomical navigation.

6. The method of claim 1 wherein the providing includes a visual representation to provide detail to a viewer.

7. The method of claim 6 wherein the visual representation is a marker.

8. The method of claim 6 wherein the visual representation includes flashing.

9. The method of claim 1 wherein the at least one device is a catheter used in an ablation procedure with the at least one electrical signal comprising a detected electrical heart signal.

10. The method of claim 1 wherein the measuring includes at least one zero signal measurement indicating a successful ablation to deaden an electrical pathway for signals in a heart.

11. The method of claim 1 wherein the measuring includes at least one live signal measurement indicating an electrical pathway for signals in a heart.

12. A non-transient computer readable medium including code stored thereon which when executed by a processor cause a system to perform a method during a validation period of a medical procedure, the method comprising:

measuring at least one electrical signal during the validation period;

processing a location of at least one device used in the measuring of the at least one electrical signal;

rendering a depiction of the medical procedure during the validation period on a display, the depiction configured to represent a portion of a patient associated with the measured at least one electrical signal, the at least one device, an area, wherein the area provides an indication of part of the portion of the patient designated to include no electrical activity; and representing the measured at least one electrical signal on the display correlated with the depiction of the medical procedure during the validation period by providing the processed location with a corresponding value of the measured at least one electrical signal, the corresponding value at least indicating a presence or absence of electrical activity at the processed location, wherein the display is configured to provide visual indication to a user of the represented measured at least one electrical signal on the display, the area, and indicating whether the processed location includes electrical activity and is within the area.

13. The computer readable medium of claim 12 wherein the at least one electrical signal is an electrical signal of a heart.

14. The computer readable medium claim 12 wherein the depiction of the medical procedure includes a rendering of a patient heart and a catheter.

15. The computer readable medium of claim 12 wherein the providing the processed location is performed using a system used for electrophysiological mapping.

16. The computer readable medium of claim 12 wherein the providing the processed location is performed using a system used for electroanatomical navigation.

17. The computer readable medium of claim 12 wherein the providing includes a visual representation to provide detail to a viewer.

18. The computer readable medium of claim 12 wherein the measuring includes at least one zero signal measurement indicating a successful ablation to deaden an electrical pathway for signals in a heart.

19. The computer readable medium of claim 12 wherein the measuring includes at least one live signal measurement indicating an electrical pathway for signals in a heart.

20. A system for performing a method during a validation period of a medical procedure, the system comprising:

a medical system for measuring at least one electrical signal in during the validation period, processing a location of at least one device used in the measuring of the at least one electrical signal, and rendering a depiction of the medical procedure during the validation period on a display, the depiction configured to represent a portion of a patient associated with the measured at least one electrical signal, the at least one device, and an area, wherein the area provides an indication of part of the portion of the patient designated to include no electrical activity, the medical system including:

a processor and memory module cooperatively coupled to correlate on the display the at least one electrical signal with the depiction of the medical procedure during the validation period by providing the processed location with a corresponding value of the measured at least one electrical signal, the corresponding value at least indicating a presence or absence of electrical activity at the processed location; and a display for providing an output that correlates the processed location with the corresponding value, wherein the display is configured to provide visual indication to a user of the represented measured at least one electrical signal on the display, the area, and indicating whether the processed location includes electrical activity and is within the area.

* * * * *